(12) United States Patent
Kusakari et al.

(10) Patent No.: US 9,700,556 B2
(45) Date of Patent: Jul. 11, 2017

(54) METHOD FOR PRODUCING INDIGO-PLANT LEAF EXTRACT

(75) Inventors: Takashi Kusakari, Takatsuki (JP); Kentaro Yamashita, Takatsuki (JP)

(73) Assignee: SUNSTAR INC., Osaka (JP)

( * ) Notice: Subject to any disclaimer, the term of this patent is extended or adjusted under 35 U.S.C. 154(b) by 0 days.

(21) Appl. No.: 14/000,748

(22) PCT Filed: Mar. 14, 2012

(86) PCT No.: PCT/JP2012/056598
§ 371 (c)(1),
(2), (4) Date: Aug. 21, 2013

(87) PCT Pub. No.: WO2012/124743
PCT Pub. Date: Sep. 20, 2012

(65) Prior Publication Data
US 2013/0331400 A1    Dec. 12, 2013

(30) Foreign Application Priority Data

Mar. 14, 2011 (JP) .................................. 2011-055942

(51) Int. Cl.
| | | |
|---|---|---|
| *A61K 36/704* | (2006.01) | |
| *A61K 31/519* | (2006.01) | |
| *A61Q 17/00* | (2006.01) | |
| *A61Q 19/00* | (2006.01) | |
| *A61K 8/97* | (2017.01) | |
| *A61K 8/49* | (2006.01) | |

(52) U.S. Cl.
CPC .......... *A61K 31/519* (2013.01); *A61K 8/4953* (2013.01); *A61K 8/97* (2013.01); *A61K 36/704* (2013.01); *A61Q 17/005* (2013.01); *A61Q 19/00* (2013.01); *A61K 2236/30* (2013.01)

(58) Field of Classification Search
None
See application file for complete search history.

(56) References Cited

U.S. PATENT DOCUMENTS

| | | |
|---|---|---|
| 5,116,997 A | 5/1992 | Kohlhaupt |
| 5,424,453 A | 6/1995 | Kohlhaupt et al. |
| 2002/0068094 A1 | 6/2002 | Aga et al. |
| 2010/0034757 A1* | 2/2010 | Fujii et al. ............ 424/58 |

FOREIGN PATENT DOCUMENTS

| | | |
|---|---|---|
| CN | 1065873 | 11/1992 |
| CN | 1081191 | 1/1994 |
| CN | 1528384 | 9/2004 |
| CN | 101701028 | 5/2010 |
| CN | 102351863 | 2/2012 |
| CN | 103497222 | 1/2014 |
| EP | 1 894 558 | 3/2008 |
| JP | 2001-031581 | 2/2001 |
| JP | 2004-189732 | 7/2004 |
| JP | 2005-281253 | 10/2005 |
| JP | 2006-241080 | 9/2006 |
| JP | 2009-149596 | 7/2009 |

OTHER PUBLICATIONS 2005, http://www.healthy-communications.com/butylene.htm.*
Supplementary European Search Report mailed Sep. 24, 2014 in corresponding European Application No. 12757148.7.
International Search Report issued Jun. 12, 2012 in International (PCT) Application No. PCT/JP2012/056598.

* cited by examiner

*Primary Examiner* — Terry A McKelvey
*Assistant Examiner* — Catheryne Chen
(74) *Attorney, Agent, or Firm* — Wenderoth, Lind & Ponack, L.L.P.

(57) ABSTRACT

An object of the present invention is to provide a tryptanthrin-containing indigo-plant leaf extract particularly suitable for application to the skin. The present invention provides a method for producing a tryptanthrin-containing indigo-plant leaf extract, the method comprising filtering a mixture of a concentrated ethanol extract of indigo-plant leaves and a polyhydric alcohol, and collecting the filtrate. The present invention further provides an indigo-plant leaf extract produced by this method.

6 Claims, 9 Drawing Sheets

Note: Concentration is defined by the volume of the solvent solution added to the concentration product.

Fig. 6

Judgment: Skin reaction assessment standard (Draize method) => Erythema and crust formation 0-4 + Edema 0-4 = Total 0-8 (grades)

<Erythema and crust formation>
0: No erythema
1: Very slight erythema (barely perceptible)
2: Well-defined erythema
3: Moderate to severe erythema
4: Severe erythema (crimson red) to slight crust formations (deep injuries)

<Edema formation>
0: No edema
1: Very slight edema (barely perceptible)
2: Slight edema (edges of area well defined by definite raising)
3: Moderate edema (raised approximately 1 millimeter)
4: Severe edema (raised more than 1 millimeter and extending beyond the area of exposure)

In each judgment, a total score equal to or larger than 1 for "erythema and crust formation" and "edema" was judged as positive, and a positive rate was obtained from the following formula.
A difference between the positive rate of the sensitization group and the positive rate of the control group was used as a sensitization rate, and sensitization evaluation classification was conducted in accordance with the criteria above.
However, sensitization of 0% was defined as no sensitization. In addition, the average grade was also calculated from the following formula.
Also, the sensitization rate was calculated from the following formula. From the sensitization rate, the sensitization evaluation classification can be obtained (table below).

Positive rate (%) = (Number of positive animals / Total number of animals) x 100

Average evaluation score = (Total score of erythema and edema) / Number of animals Sensitization rate (%) = Positive rate of sensitization group − Positive rate of control group

| Sensitization rate (%) | Grade | Classification |
|---|---|---|
| 0~8 | I | Weak |
| 9~28 | II | Mild |
| 29~64 | III | Moderate |
| 65~80 | IV | Strong |
| 81~100 | V | Extreme |

METHOD FOR PRODUCING INDIGO-PLANT LEAF EXTRACT

TECHNICAL FIELD

The present invention relates to a method for producing an indigo-plant leaf extract. More particularly, the present invention relates to a method for producing a tryptanthrin-containing indigo-plant leaf extract.

BACKGROUND ART

Leaves of indigo plants (indigo-plant leaves) contain indican (from which indigo is made). Therefore, the leaves have been preferentially used as a starting material for producing a blue dye around the world. Nowadays chemically synthesized indigo dyes are often used in industry; however, indigo-plant leaves continue to be grown for use as a dye.

In particular, leaves of *Polygonum tinctorium*, which is an indigo plant predominantly grown in Japan, are known to contain various useful ingredients in addition to indican. For example, the leaves of this indigo plant are known to contain a large amount of tryptanthrin (structural formula shown below).

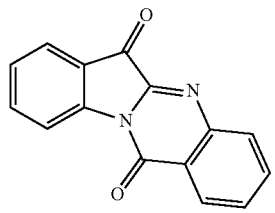

Tryptanthrin

It has been reported that tryptanthrin has an antibacterial action against fungi of the genus *Malassezia* and is therefore effective against atopic dermatitis in which fungi of the genus *Malassezia* are involved (Patent Literature (PLT) 1). Tryptanthrin has been reported to have an effect of suppressing type IV allergic reactions (Patent Literature (PTL) 2).

It is thus becoming increasingly evident that tryptanthrin exhibits useful effects particularly when applied to the skin, and demand for tryptanthrin is increasing.

As a method for extracting tryptanthrin from a indigo plant, extraction from a indigo plant by using an organic solvent is known. For example, an extraction method using dichloromethane as an extractant (Patent Literature (PTL) 1) and a method using 1,3-butylene glycol or the like as an extractant are known. (Very little tryptanthrin can be extracted with water.)

However, the use of an organic solvent is likely to result in extraction of a highly irritating ingredient. Therefore, depending on the type of organic solvent used, the obtained extract may be unsuitable for application to the skin or may contain tryptanthrin in an unstable state. No extraction method that is suitable for application to the skin has been developed yet. Another problem is that tryptanthrin fundamentally has poor light stability.

CITATION LIST

Patent Literature

PTL 1: JP2004-189732A
PTL 2: JP2006-241080A

SUMMARY OF INVENTION

Technical Problem

An object of the present invention is to provide a method for producing a tryptanthrin-containing indigo-plant leaf extract that is particularly suitable for application to the skin.

Solution to Problem

The present inventors surprisingly found that when a mixture comprising an ethanol extract of indigo-plant leaves and a polyhydric alcohol is filtered and the filtrate is collected, a tryptanthrin-containing indigo-plant leaf extract that causes no irritation to the skin (particularly no potential to cause skin sensitization) can be produced. The present inventors achieved the present invention with further improvements based on this finding.

Thus, the present invention includes, for example, the methods, extracts, and compositions listed below.

Item 1. A method for producing a tryptanthrin-containing indigo-plant leaf extract, comprising filtering a mixture of a concentrated ethanol extract of indigo-plant leaves and a polyhydric alcohol, and collecting the filtrate.

Item 2. The method according to Item 1, wherein the mixture further comprises water.

Item 3. The method according to Item 1, wherein the polyhydric alcohol is at least one glycol selected from the group consisting of 1,3-butylene glycol, propylene glycol, isoprene glycol, and pentylene glycol.

Item 4. The method according to any one of Items 1 to 3, comprising mixing the concentrated ethanol extract of indigo-plant leaves with a hydrous polyhydric alcohol, filtering the resulting mixture comprising the concentrated ethanol extract of indigo-plant leaves and the hydrous polyhydric alcohol, and collecting the filtrate.

Item 5. The method according to any one of Items 1 to 4, wherein the indigo-plant leaves are dried leaves.

Item 6. The method according to Item 5, wherein the indigo-plant leaves are sun-dried leaves.

Item 7. A tryptanthrin-containing indigo-plant leaf extract, which is obtained by the method according to any one of Items 1 to 6.

Item 8. A composition for external application to the skin comprising the tryptanthrin-containing indigo-plant leaf extract according to Item 7.

Item A. A method for improving light stability of tryptanthrin contained in an indigo-plant leaf extract, comprising filtering a mixture of a concentrated ethanol extract of indigo-plant leaves and a polyhydric alcohol, and collecting the filtrate.

Item B. A method for increasing tryptanthrin content of an indigo-plant leaf extract, comprising extracting the indigo-plant leaf extract from sun-dried indigo-plant leaves.

Item C. A method for increasing tryptanthrin content of indigo-plant leaves, comprising drying the indigo-plant leaves in the sun.

Item D. A tryptanthrin-containing indigo-plant leaf extract in the form of a solution, wherein the tryptanthrin content of the extract after 2 weeks of irradiation with white light is 80% or more of that before the irradiation.

Advantageous Effects of Invention

Tryptanthrin contained in the indigo-plant leaf extract obtained by the method for producing an indigo-plant leaf extract according to the present invention has excellent temperature stability and light stability. Furthermore, the indigo-plant leaf extract according to the present invention causes less irritation to the skin (in particular, skin sensitization), compared to conventionally produced indigo-plant leaf extracts. In addition, the indigo-plant leaf extract has excellent antimicrobial activity. Therefore, the indigo-plant leaf extract is suitable for use as a composition for external application to the skin or for use in the manufacture of compositions for external application to the skin.

Further, the method for producing an indigo-plant leaf extract according to the present invention can increase tryptanthrin content of the obtained indigo-plant leaf extract compared to conventional methods, and can also adjust the tryptanthrin content.

BRIEF DESCRIPTION OF THE DRAWINGS

FIG. 6 shows the criteria used in examining the skin sensitization of indigo-plant leaf extracts in the Test Examples.

SUMMARY OF INVENTION

Figure 1:
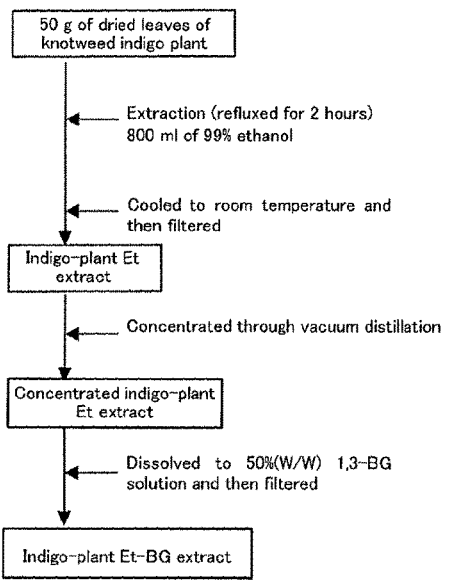
FIG. 1 is a schematic diagram of an example of the method for producing a tryptanthrin-containing indigo-plant leaf extract according to the present invention.

The present invention is explained below in more detail.

The method for producing a tryptanthrin-containing indigo-plant leaf extract according to the present invention comprises filtering a mixture comprising a concentrated ethanol extract of indigo-plant leaves and a polyhydric alcohol, and collecting the filtrate. The present invention further includes a tryptanthrin-containing indigo-plant leaf extract obtained by the production method.

Concentrated Ethanol Extract of Indigo-plant Leaves

The concentrated ethanol extract of indigo-plant leaves can be obtained by concentrating an ethanol extract of indigo-plant leaves.

The ethanol extract of indigo-plant leaves can be obtained by extracting indigo-plant leaves with ethanol. The type of indigo-plant from which indigo-plant leaves are collected is preferably an indigo-plant whose leaves contain tryptanthrin. *Polygonum tinctorium* is particularly preferable. The indigo-plant leaves to be used are preferably dried leaves. Examples of dried indigo-plant leaves include freeze-dried indigo-plant leaves, heat-dried indigo-plant leaves, and sun-dried indigo-plant leaves. The use of sun-dried indigo-plant leaves is particularly preferable because the obtained indigo-plant leaf extract has a remarkably high tryptanthrin content. The method for obtaining dried indigo-plant leaves is not particularly limited. For example, indigo-plant leaves may be dried after picking the leaves. Alternatively, after the entire plant is dried, the leaves may be collected. When the leaves are dried in the sun, the drying time may be suitably selected according to weather conditions, etc. For example, in September to November, when indigo-plant leaves are harvested in Japan, the leaves can be dried by exposure to the sun for about 2 to 7 days.

The ethanol extraction method is not particularly limited and can be suitably selected from known methods. For example, indigo-plant leaves may be extracted with ethanol under reflux. More specifically, for example, indigo-plant leaves and ethanol may be placed in a flask connected to a condenser and refluxed for about 1 to 6 hours. The amount of indigo-plant leaves to be added to ethanol can be suitably selected. For example, 1 to 10 g of indigo-plant leaves, on a dry mass basis, may be added to 100 mL of ethanol. Although hydrous ethanol (a mixture of water and ethanol) may be used for the extraction, a hydrous ethanol with a high ethanol content is preferable. For example, hydrous ethanol preferably contains ethanol in a proportion of 70% by volume or more, more preferably 90% by volume or more, even more preferably 95% by volume or more, and still more preferably 99% by volume or more.

The concentrated ethanol extract can be obtained by concentrating an ethanol extract. The method of concentrating an ethanol extract is not particularly limited, and can be suitably selected from known methods. A preferable concentration method may be, for example, distillation under reduced pressure. Specifically, a reduced-pressure distillation concentrate is suitable as the concentrated ethanol extract. The distillation under reduced pressure can be performed, for example, by using a reduced-pressure distillation concentrator or a vacuum distillation concentrator. Although the degree of concentration is not particularly limited, the ethanol extract may be concentrated, for example, to remove 90% (preferably about 90 to 99.99%) or more of the mass of the extract. As stated above, the removal can be performed, for example, by distillation under reduced pressure or by vacuum distillation. The extract may be concentrated, for example, until distillation under reduced pressure makes almost no change (no substantial change) in the mass.

Polyhydric Alcohol

Any polyhydric alcohol that is usually used for external preparations (such as cosmetics, quasi-drugs, or external drugs) can be used as the polyhydric alcohol in the present invention. Monohydric alcohols or dihydric alcohols are preferable among polyhydric alcohols. More specifically, glycol or glycerin is preferable. Specific examples thereof include 1,3-butylene glycol, propylene glycol, pentylene glycol (1,2-pentanediol), glycerol, dipropylene glycol, 1,3-propanediol, isoprene glycol (isopentyldiol), and the like. Among these, 1,3-butylene glycol, propylene glycol, pentylene glycol, and isoprene glycol are preferable, and 1,3-butylene glycol is particularly preferable. These polyhydric alcohols can be used singly or in a combination of two or more.

Mixture Comprising a Concentrated Ethanol Extract of Indigo-plant Leaves and a Polyhydric Alcohol The mixture comprising a concentrated ethanol extract of indigo-plant leaves and a polyhydric alcohol for use in the present invention can be obtained, for example, by mixing a concentrated ethanol extract of indigo-plant leaves and a polyhydric alcohol as described above. The mixing ratio of the concentrated ethanol extract to the polyhydric alcohol is not particularly limited and can be suitably selected. For example, the mass ratio of concentrated ethanol extract: polyhydric alcohol is preferably in the range of 1:16 to 2:1, more preferably 1:13 to 1:1, and even more preferably 1:10 to 1:5.

When a concentrated ethanol extract prepared by concentrating an ethanol extract is used and a relatively small amount of a polyhydric alcohol is added, the amount of filtrate obtained by the filtration step described below can be reduced, thus providing a more concentrated solution of a tryptanthrin-containing indigo-plant leaf extract. This can increase or adjust the tryptanthrin concentration in the indigo-plant leaf extract in the form of a solution and thereby enhance extraction efficiency.

The mixture comprising a concentrated ethanol extract of indigo-plant leaves and a polyhydric alcohol may further contain water. The mixture can be prepared by mixing a concentrated ethanol extract of indigo-plant leaves and a polyhydric alcohol and further adding water. Alternatively, the mixture can also be prepared by mixing a concentrated ethanol extract of indigo-plant leaves and a hydrous polyhydric alcohol (a mixture of water and a polyhydric alcohol). In either case, the mixing ratio of water to the polyhydric alcohol is not particularly limited, and can be suitably selected. The mass ratio of water to the polyhydric alcohol is preferably in the range of 25:75 to 75:25, more preferably 40:60 to 60:40, and even more preferably 45:55 to 55:45. When a hydrous polyhydric alcohol is used, the mixing ratio of water to the polyhydric alcohol in the hydrous polyhydric alcohol is preferably the mass ratio described above. After a hydrous polyhydric alcohol is mixed, water and/or a polyhydric alcohol or ethanol may be added.

As described above, the method for producing the extract according to the present invention may comprise the following four steps:
(i) extracting indigo-plant leaves with ethanol,
(ii) concentrating the ethanol extract of indigo-plant leaves,
(iii) mixing the concentrated ethanol extract of indigo-plant leaves with a polyhydric alcohol or with a hydrous polyhydric alcohol (and optionally further mixing water therewith), and
(iv) filtering the mixture of the concentrated ethanol extract of indigo-plant leaves and the polyhydric alcohol, and collecting the filtrate.

In particular, preferable embodiments of the method of the present invention include a method comprising step (iv), a method comprising steps (iii) and (iv), a method comprising steps (ii) to (iv), and a method comprising steps (i) to (iv).

Filtration

In the method for producing the extract according to the present invention, the mixture is filtered and the filtrate is collected. The method for filtering the mixture is not particularly limited, and can be suitably selected from known methods. For example, the following can be used singly or in combination: filters, pressure filters, filter presses, cooling filters, suction filters, and like filters using filter paper, filter cloth, a wedge wire screen, a urethane screen, a membrane filter, a glass filter, etc. For example, a preferable method comprises obtaining a filtrate by passing the mixture through a filter with filter cloth (e.g., Leaf Filter or Fundabac Filter) and further filtering the filtrate using a membrane filter or a glass filter. Another preferable method may be a method that can remove particles with a particle size of about 15 μm or more (preferably about 10 μm or more) by filtration, such as suction filtration using a filter paper that can retain particles with a particle size of about 10 μm or more (e.g., Qualitative Filter Paper No. 1 produced by Advantech Co., Ltd.).

The filtrate obtained by filtration can be used as a tryptanthrin-containing indigo leaf extract without subjecting the filtrate to any change. Alternatively, the obtained filtrate may be dried (for example, dried under reduced pressure or freeze-dried) to a solid (e.g., a powder), and the resulting solid may be used as a tryptanthrin-containing indigo-plant leaf extract. The scope of the present invention also includes such tryptanthrin-containing indigo-plant leaf extracts.

Tryptanthrin-containing Indigo Leaf Extract

The tryptanthrin-containing indigo-plant leaf extract of the present invention exhibits high light stability in a solution form and causes little irritation to the skin (in particular, skin sensitization); therefore, the extract is suitable for application to the skin. In particular, when the filtrate obtained by the above filtration is used in its current state as a tryptanthrin-containing indigo-plant leaf extract, the concentration has almost no change even after exposure to white light for 2 weeks. More specifically, it is preferable that at least 80% (more preferably 90% or more) of the tryptanthrin content before irradiation with white light is maintained after the irradiation. Irradiation with white light herein refers to irradiation with white light of about 10,000 lux. The irradiation can be performed by using common white fluorescent lamps.

Further, when a paste, a solid (e.g., a powder), etc., obtained by concentrating or drying the filtrate is dissolved again in a suitable solvent, the same effect as described above can be provided. As a suitable solvent, for example, at least one solvent selected from the group consisting of water, ethanol, and polyhydric alcohols mentioned above can be used.

When the extract is used in the form of a solution, the filtrate may be used as is. Alternatively, a filtrate dried (e.g., freeze-dried) or otherwise processed into a solid (e.g., a powder) may be dissolved in a suitable solvent and used.

The extract causes skin irritation (in particular, skin sensitization) whether the extract is an ethanol extract of indigo-plant leaves or a polyhydric alcohol extract of indigo-plant leaves. However, the indigo-plant leaf extract obtained by the production method of the present invention causes much less skin irritation (in particular, skin sensitization). Although a restrictive interpretation is not desired, this effect is achieved presumably for the following reason: although indigo-plant leaves contain various skin irritants, some of which are dissolved in ethanol and others of which are dissolved in a polyhydric alcohol, indigo-plant leaves contain no skin irritants that are dissolved in both ethanol and polyhydric alcohols. Based on this assumption, for use as a concentrated ethanol extract, it is considered preferable to remove ethanol from the ethanol extract as much as possible. Further, it is thought that an indigo-plant leaf extract that provides similar effects may also be produced by mixing a concentrated polyhydric alcohol extract of indigo-plant leaves and ethanol, filtering the mixture, and collecting the filtrate.

Composition for External Application to the Skin Comprising a Tryptanthrin-containing Indigo Leaf Extract The present invention further includes a composition for external application to the skin, comprising a tryptanthrin-containing indigo-plant leaf extract. The tryptanthrin-containing indigo-plant leaf extract of the present invention has excellent stability to light (light stability) and temperature stability, causes little irritation to the skin, and is suitable for application to the skin. Therefore, with use of the composition for external application to the skin according to the present invention, the effect of tryptanthrin can be preferably enjoyed. Specifically, the tryptanthrin content of the composition for external application to the skin according to the present invention has almost no reduction due to temperature or light even after long-term storage, and the composition causes little irritation to the skin and can preferably exhibit the effects of tryptanthrin, such as anti-inflammatory effects and antiallergic effects.

The composition for external application to the skin according to the present invention may be a tryptanthrin-containing indigo-plant leaf extract (including a solution form thereof) alone or may comprise, in addition to the tryptanthrin-containing indigo-plant leaf extract, optional ingredients known to be used for external application to the skin, insofar as the effect of the preset invention is not impaired. The amount of optional ingredients can be suitably selected insofar as the effect of the present invention is not impaired. For example, optional ingredients may be used in an amount of 0.1 to 99%, based on the total weight of the composition for external application to the skin. Examples of optional ingredients include known surfactants, water-soluble polymers, colorants, antioxidants, sequestrants, preservatives, pH adjusters, cooling agent, flavoring agents, moisturizers, UV absorbers, UV scatterers, anti-oxidation agents, ester oils, animal and vegetable oils, and the like. Further, other active ingredients used for external application to the skin can also be incorporated insofar as the effects of the present invention can be provided. Examples of such active ingredient include known whitening agents, anti-inflammatory agents, anti-wrinkle agents, lipolytic agents, hair growth agents, and the like.

The composition for external application to the skin of the present invention can be used, for example, as an external preparation for the skin (drug or quasi-drug) or as a cosmetic. The external preparation for the skin may be used in a dosage form suitable for application to the skin, such as gels, creams, ointments, liniments, lotions, emulsions, powders, suspending agents, aerosols, plasters, poultices, tapes, plasters, and the like. Gels, creams, and emulsions are preferable. The cosmetic may be used as a skin cosmetic such as lotions, emulsions, creams, serums, packs, makeup base lotions, makeup base creams, foundations, eye colors, cheek colors, lipsticks, and sunscreens; skin cleaners such as cleansing lotions, cleansing creams, cleansing foams, facial soaps, facial washes, and body shampoos; hair cosmetics such as hair shampoos, hair rinses, and hair treatments; bath salts; or the like. Creams, serums, and sunscreens are preferable. These products can be produced by known methods using the tryptanthrin-containing indigo-plant leaf extract optionally with the above optional ingredients and active ingredients.

EXAMPLES

The present invention is explained more specifically below. However, the present invention is not limited to the following example.

Preparation of a Tryptanthrin-containing Indigo-plant Leaf Extract

Production Example

An Outline of Production Procedures is Shown in FIG. 1.

50 g of sun-dried leaves of a *Polygonum tinctorium* (leaves collected after the entire plant was dried in the sun) was added to 800 mL (740 g) of 99.5% ethanol and extracted with ethanol under reflux for 2 hours. After the extraction, the extract was allowed to cool to room temperature and filtered through a 300-mesh stainless steel filter to remove the leaves. The obtained filtrate (ethanol extract of indigo-plant leaves) is hereinafter also referred to as "indigo-plant Et extract."

About 530 g of the indigo-plant Et extract was distilled under reduced pressure by using a rotary evaporator and concentrated until the total weight was reduced to 7.9 g or less. The obtained concentrate is hereinafter sometimes referred to as "concentrated indigo-plant Et extract."

Further, 80 mL of 50% (w/w) water-containing 1,3-butylene glycol was added to about 5 g of the concentrated indigo-plant Et extract to dissolve the extract. The obtained solution of the concentrated indigo-plant Et extract was filtered, and the filtrate was collected. The filtration was performed by suction filtration using a filter paper that can retain particles with a particle size of about 10 μm or more (Qualitative Filter Paper No.1 produced by Advantech Co., Ltd.). The procedure for obtaining the filtrate was repeated 22 times. The average weight of each obtained filtrate was about 74 g. The filtrate is hereinafter referred to as "indigo-plant Et-BG extract." The indigo-plant Et-BG extract is one example of a preferable embodiment of the tryptanthrin-containing indigo-plant leaf extract of the present invention.

Comparative Production Example

Figure 2:
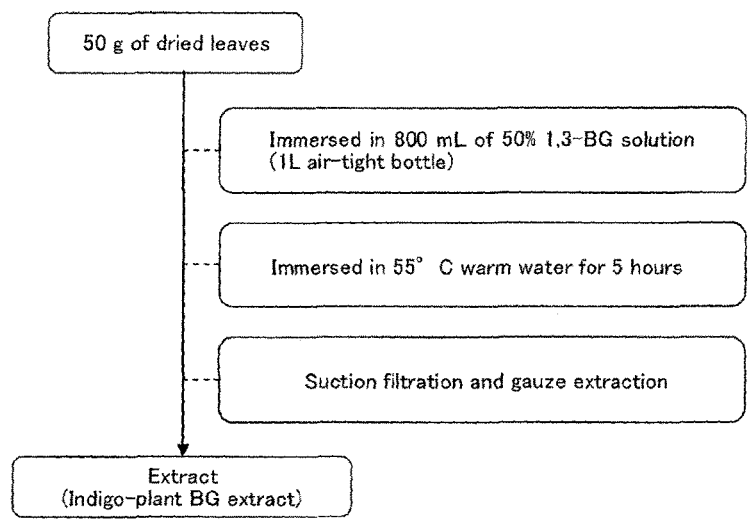
FIG. 2 is a schematic diagram of an example of a conventional method for producing a tryptanthrin-containing indigo-plant leaf extract.

An Outline of Production Procedures is Shown in FIG. 2.

Fifty grams of sun-dried leaves of *Polygonum tinctorium* (leaves collected after the entire plant was dried in the sun) were immersed in 50% (w/w) water-containing 1,3-butylene glycol and allowed to stand at 55° C. for 5 hours. The resulting product was filtered by suction filtration (using Qualitative Filter Paper No.1 produced by Advantech Co., Ltd.). The filtrate is hereinafter referred to as "indigo-plant BG extract."

Examination of the Stability of Tryptanthrin Contained in Indigo-plant Extracts

The indigo-plant Et-BG extract and the indigo-plant BG extract were stored under the four conditions (1) to (4), and the tryptanthrin content of each extract was measured 1 month, 2 months, and 3 months after the start of storage. Further, the indigo-plant Et-BG extract was measured 2 weeks after the start of the storage. For irradiation with white fluorescent lamps, each extract was irradiated with white light of about 10,000 lux. More specifically, two white fluorescent lamps (FL40SS-EX-D/37 (long shape) produced by Panasonic Corporation, length: 1198 mm, diameter of glass tube: 28 mm) were placed in parallel (distance between the lamps: about 30 cm), and each extract was placed in position between the lamps (i.e., the distance from each of the white fluorescent lamps to the extract was about 15 cm).
Condition (1): Stored at room temperature in a dark place.
Condition (2): Stored at 40° C. in a dark place.
Condition (3): Stored at −5° C. in a dark place.
Condition (4): Stored at room temperature under constant irradiation with the white fluorescent lamps.

Figure 3:
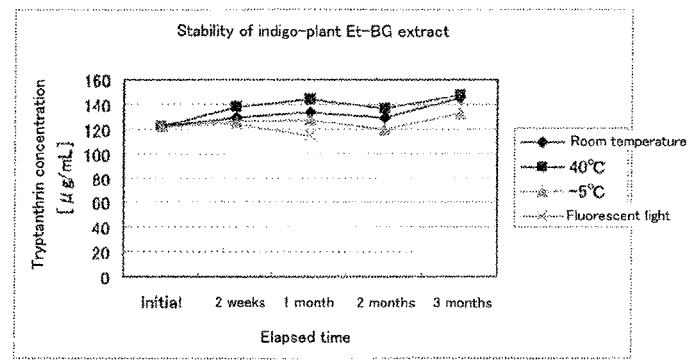
FIG. 3 shows the results of examining the stability of tryptanthrin contained in an indigo-plant Et-BG extract that was obtained by the production method shown in FIG. 1.
Figure 4:
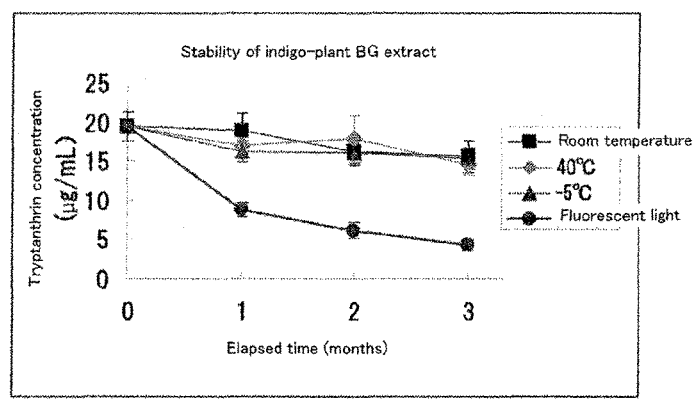
FIG. 4 shows the results of examining the stability of tryptanthrin contained in an indigo-plant BG extract that was obtained by the production method shown in FIG. 2.

The tryptanthrin content was measured using HPLC by comparison with a reference sample under the following conditions:
HPLC Conditions
Column: Cosmosil 5C18 MS-II 4.6×150 mm (5 µm)
Eluent: water/methanol=50/50
Flow rate: 1 mL/min
Column temperature: 40° C.
Detection wavelength: 254 nm
Injection volume: 20 µL FIG. 3 shows the results of the indigo-plant Et-BG extract. FIG. 4 shows the results of the indigo-plant BG extract. It was confirmed from FIGS. 3 and 4 that the indigo-plant Et-BG extract exhibits excellent light stability (stable for at least 1 month even under irradiation with light), whereas tryptanthrin is decomposed by light in the indigo-plant BG extract and the tryptanthrin content is reduced. The results also showed that both the extracts have excellent temperature stability. Further, compared to the indigo-plant BG extract, the indigo-plant Et-BG extract has a remarkably high tryptanthrin concentration. This indicates that the indigo-plant Et-BG extract is a tryptanthrin-enriched extract. It is assumed that the above condition (4) of one-month irradiation with light would correspond to about 1 year of light irradiation of the extract if the extract were presented on display as a product in a store. Thus, it is thought that the extract would exhibit sufficient light stability if commercialized.

Examination of Skin Irritation (Sensitization) of the Tryptanthrin-Containing Indigo-Plant Leaf Extract Test Example 1

Skin Sensitization of the Indigo-plant BG Extract

The skin sensitization of the indigo-plant BG extract was tested using guinea pigs (5 guinea pigs in a sensitization group and 3 guinea pigs in a control group; purchased from Japan SLC, Inc.) by the guinea pig maximization test method (GPMT method). The indigo-plant BG extract used in this test had a tryptanthrin concentration of 20.4 µg/mL. Freund's complete adjuvant (FCA) used in the test was purchased from Difco Laboratories, Inc.

The intradermal sensitization was performed in the manner described in detail as follows. Specifically, on the first day of sensitization, the sensitization group was administered the following substances (a), (b), and (c), in this order, and the control group was administered the following substances (a), (d), and (a), in this order, to right and left sides, i.e., two locations, of the neck skin of each guinea pig, in 0.1 mL portions, in such a manner that each administration position was slightly staggered. In other words, each guinea pig was intradermally administered to three sites on the right side of the neck skin and to three sites on the left side thereof. In the sensitization group, the administration interval between (a) and (b) was set to be shorter than the administration interval between (b) and (c). In the control group, the administration interval between (a) and (d) was set to be shorter than the administration interval between (d) and (a). Furthermore, the administration interval between (a) and (b) in the sensitization group and the administration interval between (a) and (d) in the control group were set to be almost equal to each other. The administration interval between (b) and (c) in the sensitization group and the administration interval between (d) and (a) in the control group were set to be almost equal to each other.

(a): Emulsion containing equal amounts of Freund's complete adjuvant (FCA) and physiological saline
(b): 30 w/w % indigo-plant BG extract solution (solvent: physiological saline),
(c): Emulsion containing equal amounts of 60 w/w % indigo-plant BG extract solution (solvent: physiological saline) and FCA
(d): Physiological saline Contact sensitization was performed as follows. At Day 7 from the intradermal sensitization (Day 0), a 2×4 cm lint cloth was impregnated with 0.2 mL of the indigo-plant Et extract and occiusively applied to the site of intradermal administration for 48 hours.

Figure 5:
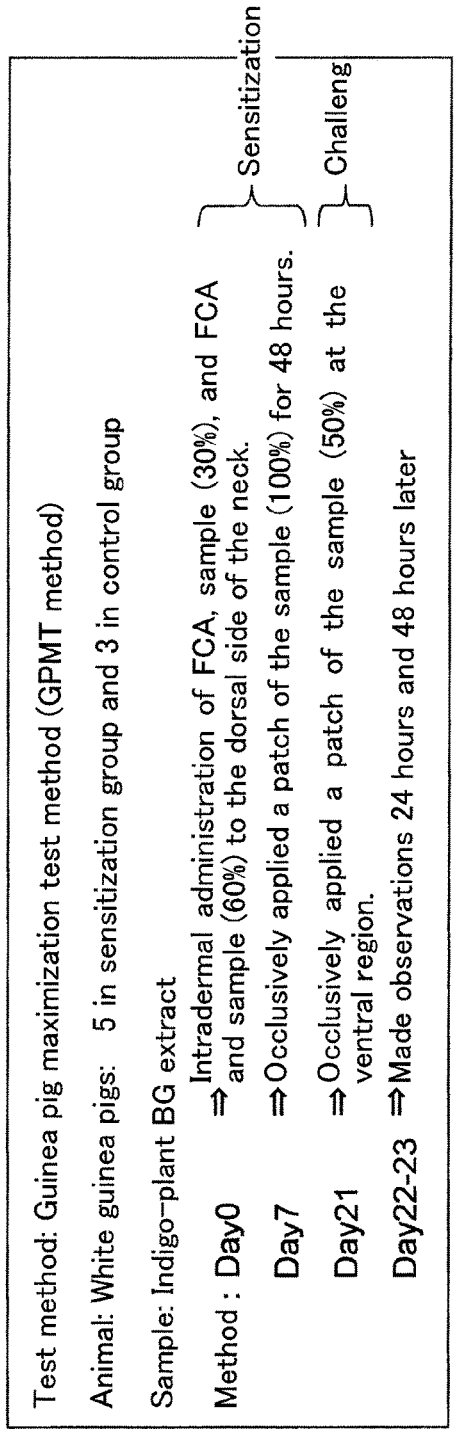
FIG. 5 outlines the procedures for examining the skin sensitization of the indigo-plant BG extract in Test Example 1.

Challenge was performed as follows. At Day 21 from the sensitization, the cloth part of a bandage for patch-testing was impregnated with 0.1 mL of a 50 w/w % solution of the indigo-plant BG extract (solvent: water for injection), and the resulting patch was occiusively applied to the ventral side of each guinea pig for 24 hours. Observation of skin reaction was conducted 24 hours and 48 hours after removing the challenge patch. An outline of the examination is shown in FIG. 5 and in the following.

Testing method: Guinea pig maximization test method (GPMT method)
Animal used: White guinea pigs (5 guinea pigs for the sensitization group and 3 guinea pigs for control groups)
Sample: Indigo-plant BG extract
Method: Day 0: FCA, the sample (30%), and a combination of FCA and the sample (60%) were intracutaneously administered to the dorsal side of the neck. (sensitization)
Day 7: The sample (100%) was occlusively applied for 48 hours. (sensitization)
Day 21: The sample (50%) was occlusively applied to the ventral side. (challenge)
Days 22 to 23: Observation was made 24 hours and 48 hours after the sensitization.

There were no abnormalities observed in the general condition of subjects during the testing period, the body weight of each subject also steadily increased. The results of skin observations (48 hours after patch removal) are shown in Table 1.

TABLE 1

| Administration sample | Sensitization group | | Control group | |
|---|---|---|---|---|
| | Positive rate (%) | Average evaluation score | Positive rate (%) | Average evaluation score |
| Indigo-plant BG extract 50% | 100 | 4.2 | 0 | 0 |

The methods for calculating the positive rate and the average evaluation score in Table 1, etc., are shown in FIG. 6 and here below.

Assessment: Skin reaction criteria (Draize method)
Erythema and Crust Formation 0 to 4+ Edema Formation 0
to 4=Total of 0 to 8 (score)
Erythema and Crust Formation
0: No erythema
1: Very slight erythema (barely perceptible)
2: Well-defined erythema
3: Moderate to severe erythema
4: Severe erythema (crimson red) to slight crust formations (deep injuries)
Edema Formation
0: No edema
1: Very slight edema (barely perceptible)
2: Slight edema (edges of area well defined by definite raising)
3: Moderate edema (raised approximately 1 millimeter)
4: Severe edema (raised more than 1 millimeter and extending beyond the area of exposure)

In each judgment, a total score equal to or higher than 1 for "Erythema and Crust Formation" and "Edema" was judged as positive, and a positive rate was obtained from the following formula. A difference between the positive rate of the sensitization group and the positive rate of the control group was used as a sensitization rate, and sensitization evaluation classification was conducted in accordance with the criteria above. However, sensitization of 0% was defined as no sensitization. The average evaluation score was also calculated from the following formula. The sensitization rate was calculated from the following formula.

Positive rate (%)=(Number of positive animals/Total number of animals)×100 Average evaluation score=(Total score of erythema and edema)/Number of animals Sensitization rate (%)=Positive rate of sensitization group−Positive rate of control group From the obtained sensitization rate, the sensitization evaluation classification can be determined as follows.

| Sensitization rate (%) | Grade | Classification |
|---|---|---|
| 0 to 8 | I | Weak |
| 9 to 28 | II | Mild |
| 29 to 64 | III | Moderate |
| 65 to 80 | IV | Strong |
| 81 to 100 | V | Extreme |

As shown above, the indigo-plant BG extract exhibited skin sensitization effects. The sensitization evaluation classification of the indigo-plant BG extract at a challenge concentration of 50 w/w % was Grade V (extreme).

Test Example 2

Skin Sensitization of Indigo-plant Et Extract and Indigo-plant Et-BG Extract

Skin sensitization of the indigo-plant Et extract and the indigo-plant Et-BG extract was examined by the adjuvant and patch test method using guinea pigs (5 guinea pigs in a sensitization group and 3 guinea pigs in a control group; purchased from Japan SLC). The tryptanthrin concentration in the indigo-plant Et extract used in this test was 17.0 μg/mL, and the tryptanthrin concentration in the indigo-plant Et-BG extract used in the test was 17.2 μg/mL. Further, the Freund's complete adjuvant (FCA) used in the test was purchased from Difco Laboratories.

Sensitization for the sensitization group was performed as follows. At Day 0 of the sensitization, an emulsion containing equal amounts of Freund's complete adjuvant (FCA) and physiological saline was intradermally administered at four corners of an administration site (neck skin), and administered spots were marked by scratching pound signs (#) thereon with a hypodermic needle. Then, by using a 2×4 cm lint cloth impregnated with 0.1 mL of the indigo-plant Et extract, an occlusive patch was applied for 24 hours such that the scratches of the four pound signs were all covered. At Day 1 and Day 2, the same procedures were performed except for the intradermal administration. At Day 7, an occlusive patch of a 2×4 cm lint cloth impregnated with 0.2 mL of the indigo-plant Et extract was applied to the same site for 48 hours. For the control group, a similar treatment was performed using water for injection instead of the extracts.

Figure 7:
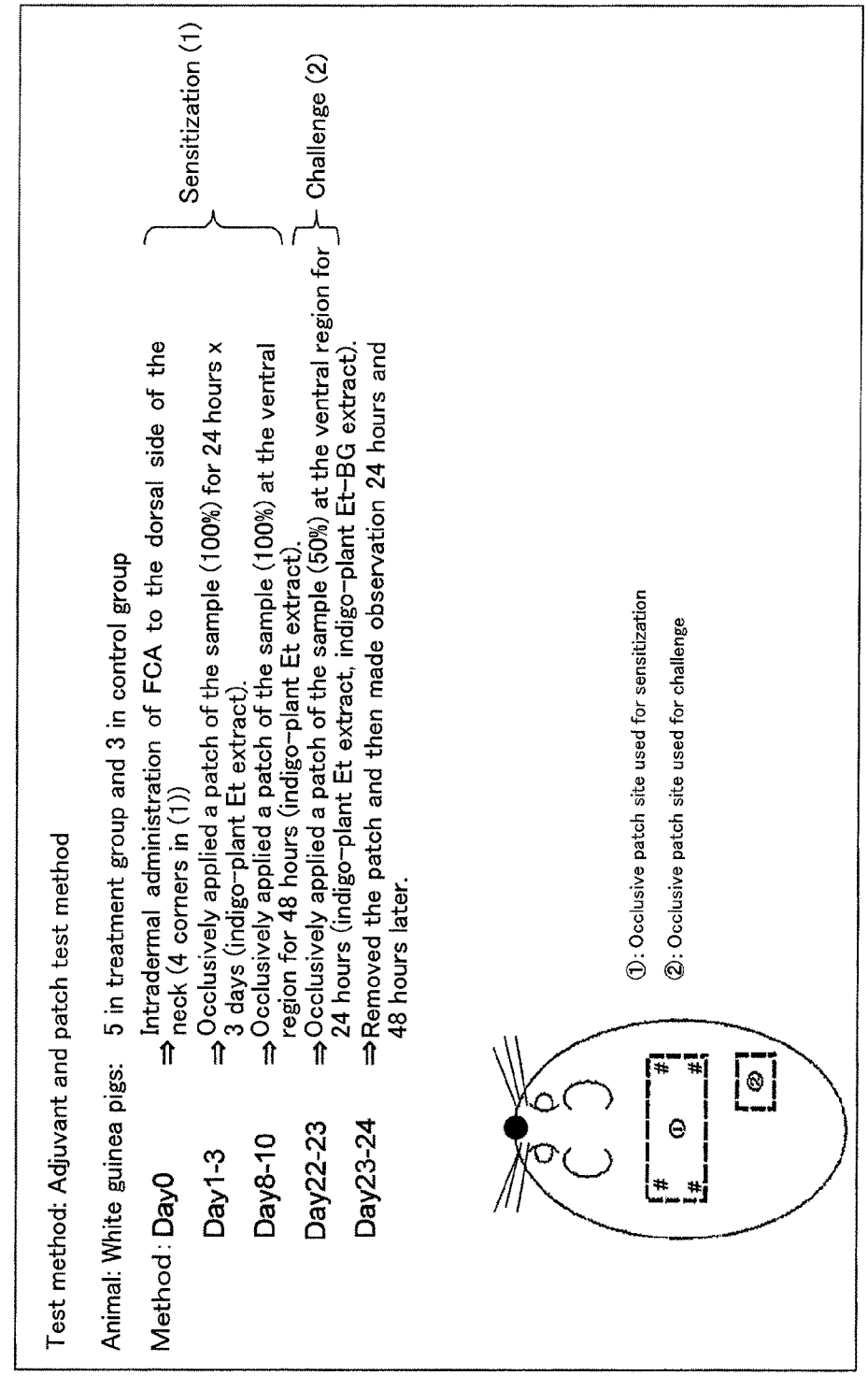
FIG. 7 outlines the procedures for examining the skin sensitization of an indigo-plant Et extract and an indigo-plant Et-BG extract in Test Example 2.

Challenge was performed as follows. At Day 21 from the sensitization, the cloth part of each bandage for patch-testing was impregnated with 0.1 mL of a 50 w/w % solution of the indigo-plant Et extract or a 50 w/w % solution of the indigo plant Et-BG extract (in both cases using water for injection as a solvent), and occlusive patches were applied to right and left ventral parts of guinea pigs for 24 hours. Observation of skin reaction was conducted 24 hours and 48 hours after removing the challenge patch. An outline of the examination is shown in FIG. 7 and here below.

Test method: Adjuvant and patch test

Used animal: White guinea pigs (5 guinea pigs for treatment group and 3 guinea pigs for control group)

Method: Day 0: Intradermal administration of FCA to the dorsal side of the neck. (In FIG. 7, administered positions are shown by pound signs at the four corners at number 1 (neck) on the drawing of a guinea pig.)

Method: Day 0: FCA was intradarmally administered to the dorsal side of the neck. (In FIG. 7, administered positions are shown by pound signs at the four corners at number 1 (neck) on the drawing of a guinea pig.)

Days 0 to 2: A patch of the sample (100%) was occlusively applied for 24 hours×3 days (indigo-plant Et extract).

Days 7 to 9: A patch of the sample (100%) was occlusively applied for 48 hours at a ventral part (indigo-plant Et extract)

Days 21 to 22: A patch of the sample (50%) was occlusively applied at a ventral part (indigo-plant Et extract, indigo plant Et-BG extract)

Days 23 to 24: The patch was removed and then observation was made 24 and 48 hours later.

The drawing of a guinea pig in FIG. 7 shows an outline of the scratches (4 locations) having a shape of a pound sign, an occlusive patch site used for the sensitization, and an occlusive patch site used for the challenge.

There were no abnormalities observed in the general state of subjects during the testing period, and the body weight of each subject also steadily increased. The results of skin observations (48 hours after patch removal) when the challenge was conducted using a 50 w/w % solution are shown in Table 2. The calculation methods, etc., for "positive rate" and "average evaluation score" in Table 2 are similar to those in Test Example 1 (shown above or in FIG. 6).

TABLE 2

| | Sensitization group | | Control group | |
|---|---|---|---|---|
| Administration sample | Positive rate (%) | Average evaluation score | Positive rate (%) | Average evaluation score |
| Indigo-plant Et extract 50% | 40 | 0.4 | 0 | 0 |
| Indigo-plant Et-BG extract 50% | 0 | 0 | 0 | 0 |

As shown above, although skin sensitization was observed with the indigo-plant Et extract, skin sensitization was not observed with the indigo-plant Et-BG extract. The sensitization evaluation classification of the indigo-plant Et extract at a challenge concentration of 50 w/w % was Grade III (moderate).

From the results above, it was confirmed that the indigo-plant BG extract and the indigo-plant Et extract have a potential to cause skin sensitization, and that the indigo-plant Et-BG extract has no potential to cause skin sensitization and therefore is preferable for application to the skin.

Examination of Various Leaves of Dried Indigo Plant

It was examined whether the amount of tryptanthrin contained in an obtained indigo-plant leaf extract changes depending on the state of the indigo plant leaf used.

An entire *Polygonum tinctorium* (part above ground) was harvested, transported in refrigeration while inserted in a water-supplying sponge, and dried as described below.
1) Fresh leaves (not dried).
2) Leaves were collected from the entire plant and then lyophilized (12 hours).
3) Leaves were collected from the entire plant and then dried by heating (80° C., 24 hours).
4) Leaves were collected from the entire plant and then sun-dried (2 days; before flowering).
5) Leaves were collected from the entire plant and then sun-dried (2 days; after flowering).
6) The entire plant was sun-dried (7 days) and then leaves were collected.

In all processes, 40 g of fresh leaves of a knotweed indigo plant were used. After the drying, about 7.5 g of dried leaves were obtained in all the cases.

Next, by using fresh leaves or dried leaves described above in items 1) to 6), and commercially available dried indigo-plant leaves, indigo-plant Et extracts were produced in a manner similar to the method described in Production Example 1 above. Then, the amount of tryptanthrin contained in each extract was measured using the HPLC conditions described above.

Figure 8:
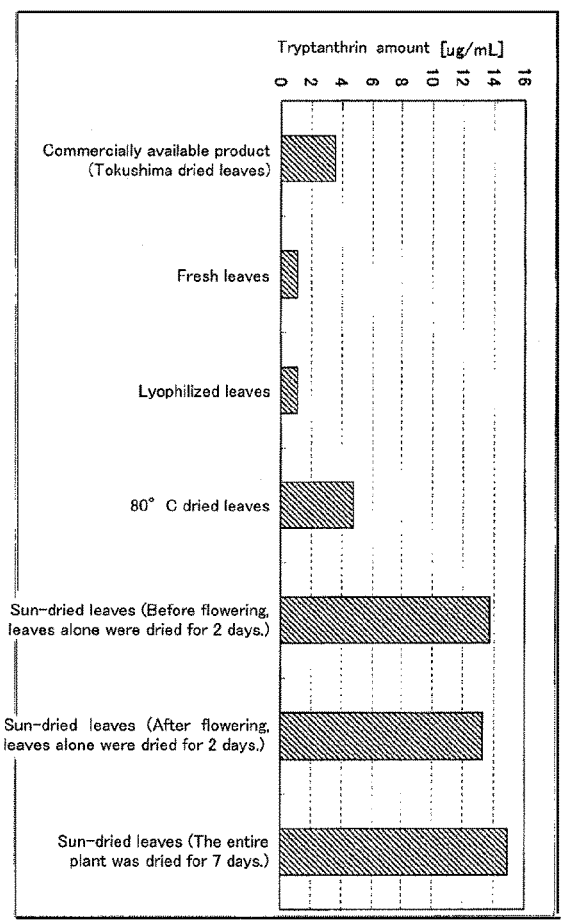
FIG. 8 shows the test results regarding whether tryptanthrin content of the obtained indigo-plant leaf extract varies depending on the condition of indigo-plant leaves.

The results are shown in FIG. 8. From the results, it was revealed that an extract containing a larger amount of tryptanthrin can be obtained by using dried leaves rather than fresh leaves, an extract containing a significantly larger amount of tryptanthrin can be obtained by using sun-dried leaves, and the amount of tryptanthrin contained in indigo-plant leaves can be improved by drying the indigo-plant leaves under sunlight.

Examination of Antibacterial Activity of Indigo-plant Leaf Extract

Strengths of antibacterial activities of various indigo-plant leaf extracts were examined as described below. SCD liquid medium and SCDLP agar medium used in the examination were purchased from Merck Ltd. Specifically, "soybean casein digest" (produced by Merck Ltd.) was used as the SCD liquid medium, and "soybean casein digest agar with lecithin and polysorbate 80" (produced by Merck Ltd.) was used as the SCDLP agar medium. In addition, the "water extract of indigo plant" used in the examination is an indigo-plant leaf extract obtained using water instead of 50%(w/w) water-mixed 1,3-butylene glycol used in the method for producing the indigo-plant BG extract (i.e., the method set forth in the Comparative Production Example above).

*Staphylococcus aureus* (NBRC 13276) was suspended in 5 mL of SCD liquid medium, and cultured overnight at 30° C. by shaking. This culture was diluted using SCD liquid medium so that it had 0.5 McFarland (equivalent to a viable cell count concentration of approximately $1.5 \times 10^8$ CFU/mL). The obtained dilution was further diluted 100-fold using SCD liquid medium to obtain a bacteria suspension liquid.

Figure 9:
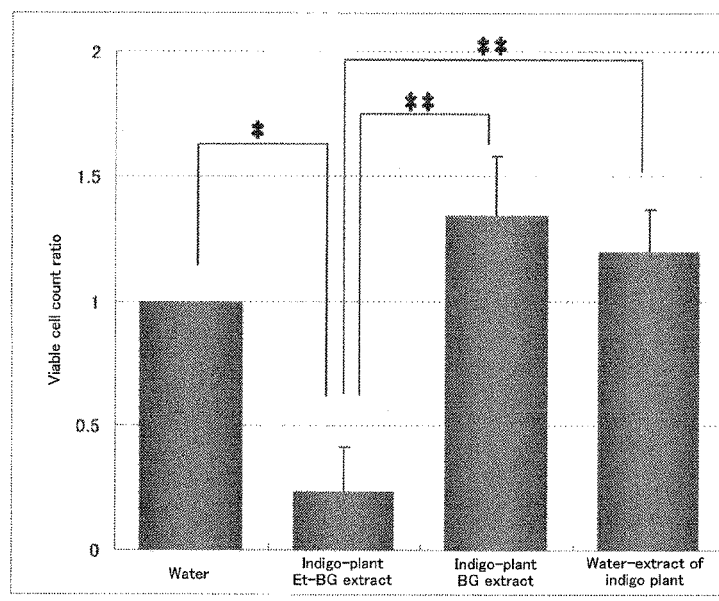
FIG. 9 is a graph comparing the viable cell ratios obtained by culturing *Staphylococcus aureus* in media each containing one of the following: an indigo-plant Et-BG extract, an indigo-plant BG extract, an water extract of indigo-plant, and water.

150 μL of the indigo-plant Et-BG extract, the indigo-plant BG extract, the water extract of indigo plant, or water was added to 4.5 mL of SCD liquid medium dispensed in a test tube, and SCD liquid medium was further added thereto to obtain a total volume of 5 mL. 50 μL of the bacteria suspension liquid was added to the obtained extract-containing medium, and the mixture was stirred thoroughly, and cultured for 24 hours at 30° C. by shaking. The liquid culture medium obtained in this manner was used as a cultured-bacteria liquid. The cultured-bacteria liquid was serially diluted 10-fold per dilution using a 0.85% sodium chloride solution, and 100 μL of each serially diluted solution was plated on SCDLP agar medium and cultured for 1 day at 30° C. Specifically, the cultured-bacteria liquid containing the indigo-plant Et-BG extract was diluted $10^4$-fold or $10^5$-fold, and each of the solutions thus obtained was plated and cultured on two agar medium plates (total of 4 plates). Culturing of the cultured-bacteria liquids containing other extracts or water was conducted similarly except that the liquids were diluted $10^5$-fold or $10^6$-fold. The number of colonies generated on the surface of the medium was counted, and a viable cell count (CFU/mL) contained in 1 mL of a cultured-bacteria liquid was obtained based on the measured colony count. FIG. 9 is a graph showing the relative ratios of viable cell counts obtained using each of the indigo-plant leaf extracts, with the viable cell count obtained using water instead of the indigo-plant leaf extracts being defined as 1. In FIG. 9, a single asterisk (*) indicates $p < 0.05$, and double asterisks (**) indicates $p < 0.005$. No significant differences were observed between when culturing was conducted by adding the indigo-plant BG extract or the water extract of indigo plant to medium, and when culturing was conducted by adding water to medium.

From the results above, it was revealed that the indigo-plant Et-BG extract has extremely superior antibacterial activity.

Formulation Examples of the composition for external application to the skin of the present invention are shown below. Each of the Formulation Examples was prepared in accordance with a method commonly used in the art. In the Formulation Examples, "indigo-plant extract" refers to the indigo-plant Et-BG extract; and % represents mass %.

TABLE 3

Formulation Example 1: Beauty Lotion

| Ingredient | Blend amount (%) |
|---|---|
| Indigo-plant extract | 10 |
| Concentrated glycerin | 1 |

TABLE 3-continued

Formulation Example 1: Beauty Lotion

| Ingredient | Blend amount (%) |
| --- | --- |
| Squalane | 2 |
| Olive oil | 2 |
| Jojoba oil | 1.8 |
| Pentaerythrityl tetraoctanoate | 1 |
| Polyoxyethylene oleyl ether | 0.8 |
| Methyl polysiloxane | 0.5 |
| Methyl parahydroxybenzoate | 0.1 |
| Carboxyvinyl polymer | 0.2 |
| Xanthan gum | 0.05 |
| Potassium hydroxide | Adequate quantity (adjusted to a pH of 7.5) |
| Purified water | Remaining portion |
| Total | 100 |

TABLE 4

Formulation Example 2: Face Lotion

| Ingredient | Blend amount (%) |
| --- | --- |
| Indigo-plant extract | 1 |
| Ethanol | 5 |
| Concentrated glycerin | 10 |
| 1,3-butylene glycol | 5 |
| Sodium hyaluronate | 0.2 |
| Polyoxyethylene hydrogenated castor oil (60 EO) | 0.6 |
| Methyl parahydroxybenzoate | 0.1 |
| Citric acid | 0.06 |
| Sodium citrate | 0.08 |
| Purified water | Remaining portion |
| Total | 100 |

TABLE 5

Formulation Example 3: Skin Cream

| Ingredient | Blend amount (%) |
| --- | --- |
| Indigo-plant extract | 5 |
| Concentrated glycerin | 10 |
| Squalane | 8 |
| Olive oil | 4 |
| Macadamia nuts oil | 4 |
| Stearic acid | 3 |
| Cetanol | 3 |
| Lipophilic glyceryl monostearate | 3 |
| Polyglyceryl monostearate | 2 |
| Methyl parahydroxybenzoate | 0.2 |
| Potassium hydroxide | Adequate quantity (adjusted to a pH of 6.5) |
| Purified water | Remaining portion |
| Total | 100 |

TABLE 6

Formulation Example 4: UV Cream

| Ingredient | Blend amount (%) |
| --- | --- |
| Cyclic silicone (n = 5) | 15 |
| Fine zinc oxide particle | 10 |
| Fine titanium oxide particle | 5 |
| Squalane | 3 |
| Hazelnut oil | 2 |
| Olive oil | 1 |

TABLE 6-continued

Formulation Example 4: UV Cream

| Ingredient | Blend amount (%) |
| --- | --- |
| Behenyl alcohol | 2 |
| Polyglyceryl diisostearate | 2 |
| Indigo-plant extract | 1 |
| Sodium chloride | 0.5 |
| 1,3-butylene glycol | 5 |
| Methyl parahydroxybenzoate | 0.1 |
| Purified water | Remaining portion |
| Total | 100 |

TABLE 7

Formulation Example 5: Face Wash

| Ingredient | Blend amount (%) |
| --- | --- |
| Indigo-plant extract | 0.5 |
| Potassium laurate | 5 |
| Potassium myristate | 15 |
| Potassium palmitate | 10 |
| Potassium stearate | 10 |
| Polyethylene glycol | 5 |
| Palm oil fatty acid diethanolamide | 2 |
| Polyoxyethylene palm oil fatty acid glyceryl | 1 |
| Concentrated glycerin | 10 |
| Methyl parahydroxybenzoate | 0.1 |
| Purified water | Remaining portion |
| Total | 100 |

TABLE 8

Formulation Example 6: Cleansing Agent

| Ingredient | Blend Amount (%) |
| --- | --- |
| Indigo-plant extract | 1 |
| POE lauryl sulfosuccinic acid Mg (3EO) | 2 |
| Tetra oleic acid POE (40) sorbitol | 1 |
| Self-emulsifiable glyceryl monostearate | 2 |
| Stearic acid | 4 |
| Cetanol | 2 |
| Cetyl palmitate | 2 |
| Paraffin (135° F.) | 2 |
| Liquid paraffin | 30 |
| Isopropyl palmitate | 10 |
| Tri-2-glyceryl ethylhexanoate | 10 |
| Methyl parahydroxybenzoate | 0.1 |
| 1,3-butylene glycol | 5 |
| Perfume | 0.1 |
| Citric acid | Adequate quantity (adjusted to a pH of 5.0) |
| Purified water | Remaining portion |
| Total | 100 |

The invention claimed is:

1. A method for producing a tryptanthrin-containing indigo-plant leaf extract, comprising sequentially performing the following steps (i) to (v):
   (i) extracting indigo-plant leaves with ethanol, followed by removing the indigo-plant leaves from the ethanol to obtain an ethanol extract of indigo-plant leaves, wherein the indigo-plant leaves have been removed;
   (ii) concentrating the ethanol extract of indigo-plant leaves to obtain a concentrated ethanol extract of indigo-plant leaves;
   (iii) mixing the concentrated ethanol extract of indigo-plant leaves with polyhydric alcohol to obtain a mixture of the concentrated ethanol extract of indigo-plant leaves and the polyhydric alcohol;

(iv) filtering the mixture of the concentrated ethanol extract of indigo-plant leaves and the polyhydric alcohol to obtain a filtrate, wherein the filtrate is the tryptanthrin-containing indigo-plant leaf extract; and (v) collecting the filtrate.

2. The method according to claim 1, wherein the mixture further comprises water.

3. The method according to claim 1, wherein the polyhydric alcohol is at least one glycol selected from the group consisting of 1,3-butylene glycol, propylene glycol, isoprene glycol, and pentylene glycol.

4. The method according to claim 1, wherein the polyhydric alcohol is a hydrous polyhydric alcohol.

5. The method according to claim 1, wherein the indigo-plant leaves are dried leaves.

6. The method according to claim 5, wherein the indigo-plant leaves are sun-dried leaves.

\* \* \* \* \*